(12) United States Patent
Sheu et al.

(10) Patent No.: US 8,552,195 B2
(45) Date of Patent: Oct. 8, 2013

(54) METHOD FOR MAKING DONEPEZIL

(75) Inventors: Kuen-Wang Sheu, Taoyuan Hsien (TW); Shu-Fen Huang, Taoyuan Hsien (TW)

(73) Assignee: Taiwan Biotech Co., Ltd., Taoyuan Hsien (TW)

( * ) Notice: Subject to any disclaimer, the term of this patent is extended or adjusted under 35 U.S.C. 154(b) by 164 days.

(21) Appl. No.: 13/198,775

(22) Filed: Aug. 5, 2011

(65) Prior Publication Data
US 2013/0035490 A1 Feb. 7, 2013

(51) Int. Cl.
*C07D 211/32* (2006.01)
(52) U.S. Cl.
USPC ............ 546/206; 546/205; 546/238; 546/324
(58) Field of Classification Search
USPC .................................. 546/205, 206, 238, 324
See application file for complete search history.

(56) References Cited

U.S. PATENT DOCUMENTS

| | | | |
|---|---|---|---|
| 7,332,606 B2 * | 2/2008 | Imai .............................. | 546/206 |
| 7,511,148 B2 * | 3/2009 | Nambiar et al. ........... | 546/269.7 |
| 8,124,783 B2 * | 2/2012 | Dubey et al. .................. | 546/342 |
| 2009/0253746 A1 * | 10/2009 | Soldevilla Madrid ........ | 514/319 |
| 2010/0022615 A1 * | 1/2010 | Fegley et al. ................. | 514/425 |

OTHER PUBLICATIONS

Barasubramanian et al. "Sodium dithionite" p. 1-8 (1995).*
Zakrzewski et al. "Mechanism of reduction . . . " J. Biol. Chem. v.242(24) p. 5661-5666(1967).*

* cited by examiner

*Primary Examiner* — Celia Chang
(74) *Attorney, Agent, or Firm* — Fishman & Associates, LLC.

(57) ABSTRACT

The method in accordance with the present invention has: mixing E2M, an organic solvent, a weak base, sodium dithionite, and a phase transfer catalyst to obtain an E2M mixture solution; heating the E2M mixture solution and adding water to obtain a heated E2M aqueous solution having an organic layer; and extracting the organic layer from the heated E2M aqueous solution, and condensing and drying the organic layer to obtain donepezil. Employing sodium dithionite as a reducing agent improves safety over hydrogen gas used in conventional methods and lowers the cost in contrast to the conventional noble metal catalysts that are extremely expensive. Furthermore, the method of the present invention requires only 60 minutes of reaction time to synthesize donepezil with a promising yield more than 85%, which greatly raises the efficiency and economic value of the manufacture of donepezil.

3 Claims, 2 Drawing Sheets

METHOD FOR MAKING DONEPEZIL

BACKGROUND OF THE INVENTION

1. Field of the Invention

The present invention relates to a method for making donepezil, especially to a method for making donepezil using a low-cost reducing agent, sodium dithionite ($Na_2S_2O_4$), for shortening reaction time and improving safety.

2. Description of the Prior Art

Donepezil is one of the most important drugs for treating Alzheimer's disease and has been approved by FDA in 1996 under the brand Aricept®.

The conventional method for making donepezil starts with a reduction reaction by using (E)-2-((1-benzylpiperidine-4-yl)methylene)-5,6-dimethoxy-2,3-dihydro-1H-inden-1-one (hereinafter denoted as "E2M") as a precursor, whose structure is as shown in formula 1.

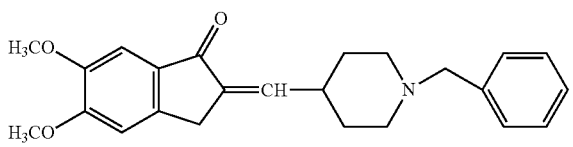

Formula 1

Donepezil, 2-((1-benzylpiperidine-4-yl)-5,6-dimethoxy-2,3-dihydro-1H-inden-1-one, has a structure as shown in Formula 2.

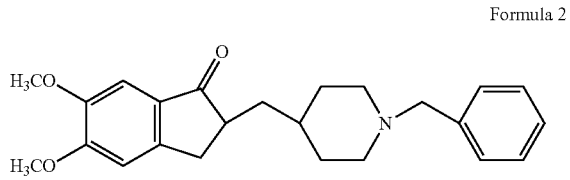 [SMILES: COc1cc2c(cc1OC)C(=O)C(CC1CCN(Cc3ccccc3)CC1)C2]

Formula 2

With reference to U.S. patent publications 2007/0088055 and 2009/0253746, in these methods the "carbon=carbon" double bond of E2M is reduced to the "carbon-carbon" single bond of donepezil with catalyst. The catalysts used in the references are hydrogen gas ($H_2$) and palladium (Pd)/aluminum(III) oxide ($Al_2O_3$), and hydrogen gas and platinum (Pt)/carbon (C) respectively, both of which allow hydrogen on the surface of a noble metal, palladium or platinum reducing the "carbon=carbon" double bond of E2M to the "carbon-carbon" single bond, resulting in donepezil.

Utilizing the conventional methods not only acutely raises safety concerns by employing hydrogen for reduction, but also raises the cost by using the noble metal such as palladium or platinum. In addition, the reaction times of the inefficient catalyzed reactions as disclosed in the aforementioned references are respectively 3 hours and 7 hours.

To overcome the shortcomings, the present invention provides a method for making donepezil to mitigate or obviate the aforementioned problems.

SUMMARY OF THE INVENTION

The main objective of the invention is to provide a method for making donepezil.

The method in accordance with the present invention comprises: mixing E2M, an organic solvent, a weak base, sodium dithionite, and a phase transfer catalyst to obtain an E2M mixture solution; heating the E2M mixture solution and adding water to obtain a heated E2M aqueous solution having an organic layer; and extracting the organic layer from the heated E2M aqueous solution, and condensing and drying the organic layer to obtain donepezil.

Employing sodium dithionite as a reducing agent improves safety over hydrogen gas used in conventional methods and lowers the cost in contrast to the conventional noble metal catalysts that are extremely expensive. Furthermore, the method of the present invention requires only 60 minutes of reaction time to synthesize donepezil with a promising yield more than 85%, which greatly raises the efficiency and economic value of the manufacture of donepezil.

Other objectives, advantages and novel features of the invention will become more apparent from the following detailed description when taken in conjunction with the accompanying drawings.

DETAILED DESCRIPTION OF THE PREFERRED EMBODIMENTS

Example 1

In this example a method for preparing E2M, the precursor for making donepezil, is demonstrated. The method for preparing E2M comprises the following steps:

1. Obtaining a potassium hydroxide aqueous solution by dissolving sodium hydroxide in water;
2. Adding 1) tetrabutylammonium bromide, 2) 5,6-Dimethoxy-1-indanone, 3) dichloromethane, and 4) N-benzylpiperidine-4-carboxyaldehyde into the aforementioned potassium hydroxide aqueous solution to obtain a potassium hydroxide mixture solution;
3. Heating the potassium hydroxide mixture solution while stirring to allow reaction for obtaining a heated potassium hydroxide mixture solution that has an organic layer; and
4. Extracting the organic layer of the heated potassium hydroxide mixture solution with methylbenzene (toluene) to obtain a product and crystallizing and filtering the product to obtain E2M.

In the instant example, the foregoing steps were specifically performed as follows.

1. 11.11 grams or 0.0535 mol of N-benzylpiperidine-4-carboxyaldehyde having a structure as shown in Formula 3, and 10 grams or 0.051 mol of 5,6-Dimethoxy-1-indanone having a structure as shown in Formula 4 were prepared.

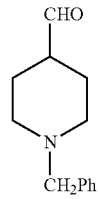

Formula 3

-continued

Formula 4

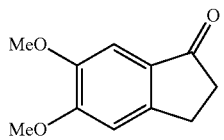

13.46 grams or 0.2039 mol of potassium hydroxide (KOH), 100 ml of water, 8.39 grams or 0.0255 mol of tetrabutylammonium bromide, and 80 ml of dichloromethane were prepared, wherein the mole ratio of aforementioned compounds was:

N-benzylpiperidine-4-carboxyaldehyde:5,6-Dimethoxy-1-indanone:potassium hydroxide:tetrabutylammonium bromide=1.05:1:4:0.5.

In a container potassium hydroxide was dissolved in water, added with tetrabutylammonium bromide, dichloromethane, N-benzylpiperidine-4-carboxyaldehyde and 5,6-Dimethoxy-1-indanone to form a mixture, and then the mixture was stirred and heated to allow reacting at 38 degrees Celsius for 1.5 hours to obtain a heated potassium hydroxide mixture solution, wherein the tetrabutylammonium bromide was employed as a phase transfer catalyst.

2. An organic layer was separated from an aqueous layer of the heated potassium hydroxide mixture solution, washed with 80 ml of water, dehydrated with anhydrous magnesium sulfate, and condensed and dried.

3. 100 ml of methylbenzene was added to the organic layer to obtain a mixture. The mixture was stirred and heated to 78 degrees Celsius to allow dissolution and clearance. Gradually the temperature was lowered to 68 degrees Celsius to allow generation of crystals. Stirring of the mixture was continued for 30 minutes and the temperature was further lowered to room temperature. The mixture was ice-bathed for 2 hours and filtered and a powder was obtained.

Figure 1:
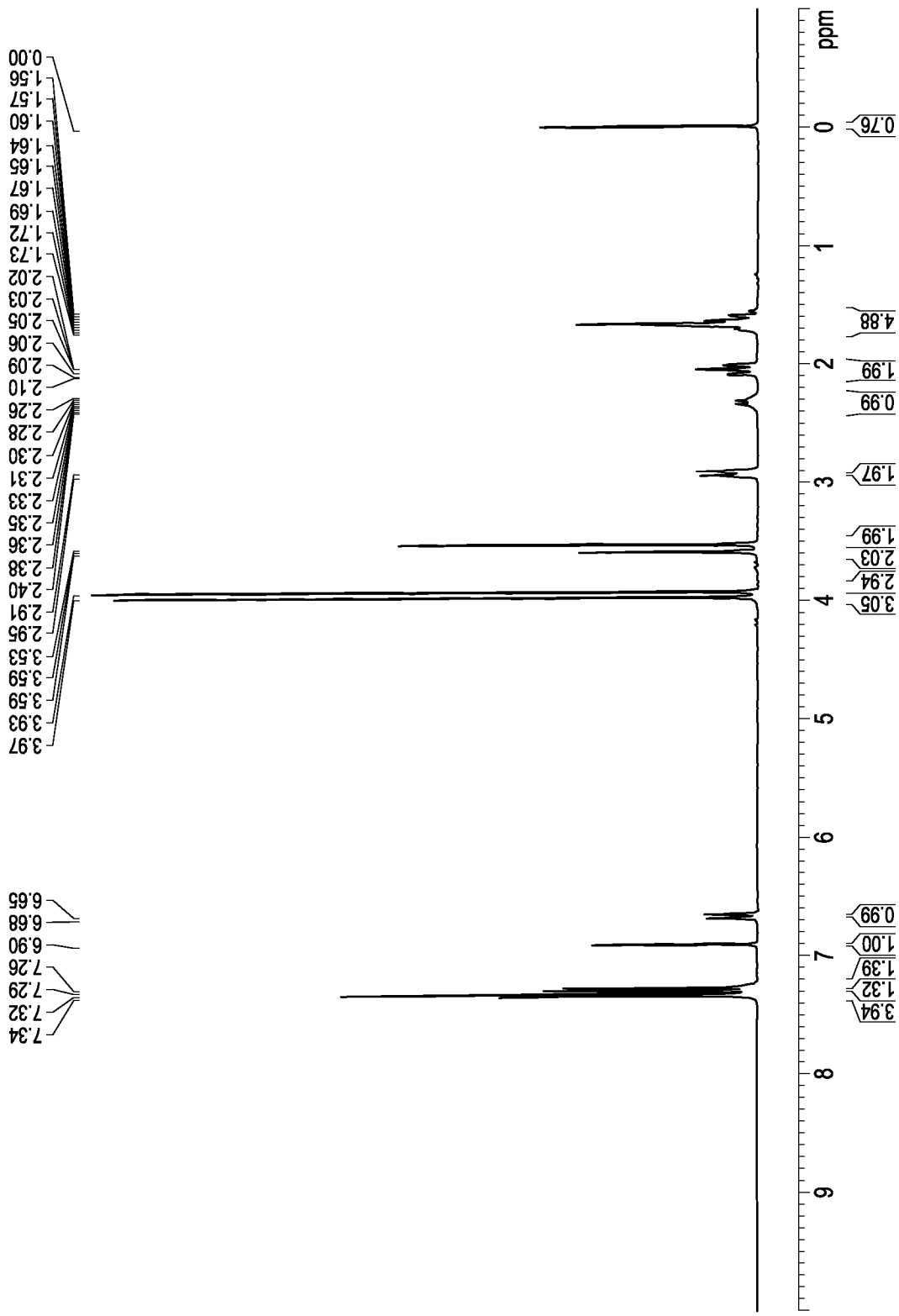
FIG. 1 is a hydrogen-1 NMR (proton NMR) spectrum of E2M of example 1.

With reference to FIG. 1, by hydrogen-1 NMR analysis the powder is identified as E2M. With the method as demonstrated in the instant example, the molecular weight of E2M is 377.5 and the yield of E2M is more than 90% while the purity thereof reaches 98.551%.

The reaction performed in the instant example is shown in Reaction 1.

Reaction 1

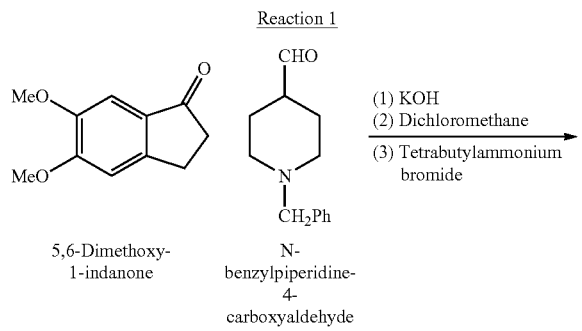

5,6-Dimethoxy-1-indanone

N-benzylpiperidine-4-carboxyaldehyde (1) KOH
(2) Dichloromethane
(3) Tetrabutylammonium bromide -continued

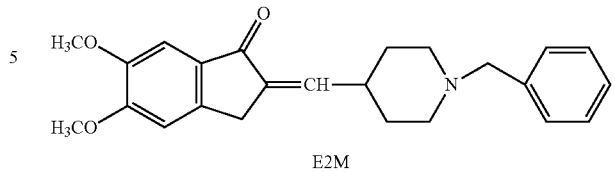

E2M

Example 2

In this example a method for making donepezil with E2M is demonstrated. The method for making donepezil comprises the following steps:

1. Mixing methylbenzene, E2M, sodium hydrogen carbonate, sodium dithionite and tetrabutylammonium bromide to obtain an E2M mixture solution;

2. Heating the E2M mixture solution and adding water to allow reaction for obtaining a heated E2M aqueous solution having a methylbenzene layer; and 3. Extracting the methylbenzene layer from the heated E2M aqueous solution, and condensing and drying the methylbenzene layer to obtain donepezil.

In the instant example, the foregoing steps were specifically performed as follows.

1. At room temperature 1 gram or 0.0026 mol of E2M powder and 10 ml of methylbenzene were placed into a container, and further added with 4.01 grams or 0.0472 mol of sodium hydrogen carbonate, 4.83 grams or 0.0236 mol of sodium dithionite and 0.43 grams or 0.0013 mol of tetrabutylammonium bromide, wherein the molar ratio of E2M:sodium hydrogen carbonate:sodium dithionite:tetrabutylammonium bromide was 1:18:9:0.5.

Methylbenzene, E2M, sodium hydrogen carbonate, sodium dithionite and tetrabutylammonium bromide were added in the container, the temperature was raised to 70 degrees Celsius and 20 ml of water was added at a rate of 5 ml/min, allowing reacting for 60 minutes, and then heating was ceased to stop the reaction to obtain a heated E2M aqueous solution.

2. A methylbenzene layer was taken out from the heated E2M aqueous solution, washed with 10 ml of water, and condensed and dried.

3. A powder was obtained from the condensed and dried methylbenzene layer.

Figure 2:
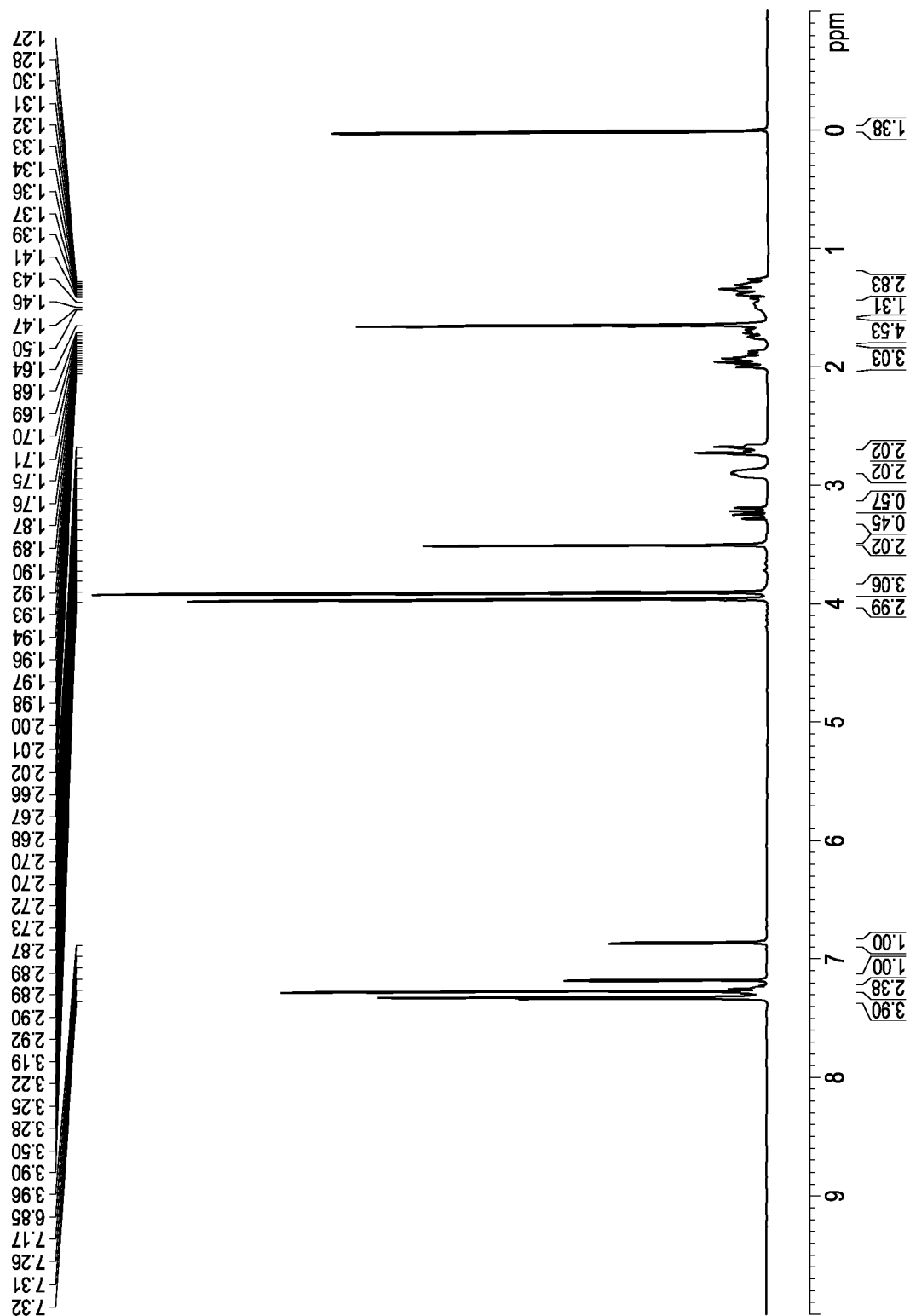
FIG. 2 is a hydrogen-1 NMR spectrum of donepezil of example 2.

With reference to FIG. 2, by hydrogen-1 NMR analysis the powder is identified as donepezil. With the method as demonstrated in the instant example, the molecular weight of donepezil is 379.5 and the yield of donepezil is more than 85% while the purity of the donepezil produced reaches 99.756%.

The reaction performed in the instant example is shown in Reaction 2.

Reaction 2

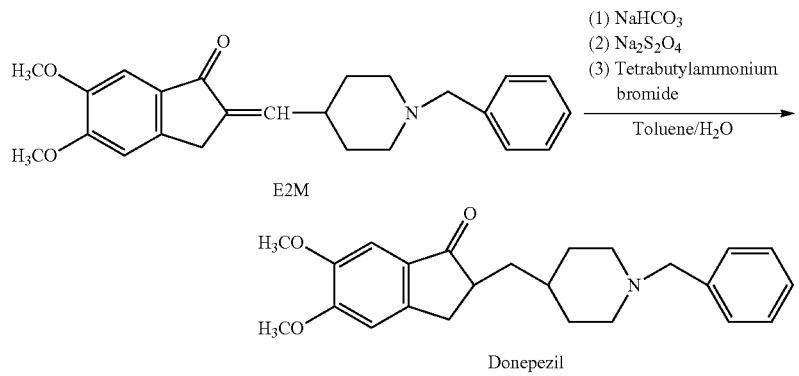

The instant example shows that sodium dithionite is a safer reducing agent than hydrogen gas. Furthermore, sodium dithionite is more stable in a weak basic environment, which may be provided in the heated E2M aqueous solution with the addition of sodium hydrogen carbonate in order to facilitate the reaction. The synthesis reaction is a two-phase reaction wherein sodium dithionite is dissolved only in an aqueous phase instead of the organic phase (methylbenzene). E2M is, however, an organic compound and dissolved only in the organic phase, thus tetrabutylammonium bromide, the phase transfer catalyst, is added to allow the reaction. In summary, as shown in the instant example, the reducing agent, sodium dithionite, employed in the present invention is low-cost and safe, and the synthesis performed therewith requires only a short reaction time of 60 minutes.

Example 3

The instant example demonstrates another method for making donepezil with E2M. The method comprises the following steps:

1. Mixing ethyl acetate, E2M, sodium hydrogen carbonate, sodium dithionite, tetrabutylammonium bromide and water to obtain an E2M mixture solution;
2. Heating the E2M mixture solution to obtain a heated E2M aqueous solution having an organic layer; and
3. Extracting the organic layer from the heated E2M aqueous solution, and condensing and drying the organic layer to obtain donepezil.

In the instant example, the foregoing steps were specifically performed as follows:

1. At room temperature 1 gram or 0.0026 mol of E2M powder and 15 ml of ethyl acetate were placed into a container, and further added with 1.35 grams or 0.0159 mol of sodium hydrogen carbonate, 1.09 grams or 0.0053 mol of sodium dithionite and 0.44 grams or 0.0013 mol of tetrabutylammonium bromide, wherein the mole ratio of E2M:sodium hydrogen carbonate:sodium dithionite:tetrabutylammonium bromide was 1:6:2:0.5.

Ethyl acetate, E2M, sodium hydrogen carbonate and tetrabutylammonium bromide were added in the container, further added with 15 ml of water, the temperature was raised to 65 degrees Celsius, sodium dithionite was added, allowing reacting for 30 minutes and then heating was ceased to stop the reaction to obtain a heated E2M aqueous solution.

2. An organic layer was taken out from the heated E2M aqueous solution, washed with water, dehydrated with anhydrous magnesium sulfate and then condensed and dried to obtain a powder from the condensed and dried organic layer.

With the method as demonstrated in the instant example, the molecular weight of donepezil is 379.5 and the yield of donepezil is 88% while the purity of the donepezil produced reaches 99.802%.

The reaction performed in the instant example is shown in Reaction 3.

Reaction 3

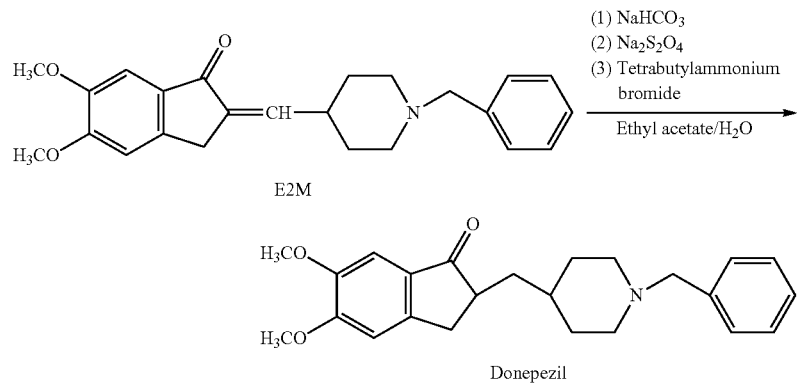

Example 4

The instant example demonstrates another method for making donepezil with E2M. The method comprises the following steps:

1. Mixing isobutanol (isobutyl alcohol or 2-Methylpropan-1-ol), E2M, sodium hydrogen carbonate, sodium dithionite, tetrabutylammonium bromide and water to obtain an E2M mixture solution;
2. Heating the E2M mixture solution to obtain a heated E2M aqueous solution having an organic layer; and
3. Extracting the organic layer from the heated E2M aqueous solution, and crystallizing and filtering the organic layer to obtain donepezil.

In the instant example, the foregoing steps were specifically performed as follows:

1. At room temperature 1 gram or 0.0026 mol of E2M powder and 15 ml of isobutanol were placed into a container, and further added with 2.7 grams or 0.0318 mol of sodium hydrogen carbonate, 1.09 grams or 0.0053 mol of sodium dithionite and 0.44 grams or 0.0013 mol of tetrabutylammonium bromide, wherein the mole ratio of E2M:sodium hydrogen carbonate:sodium dithionite:tetrabutylammonium bromide was 1:12:2:0.5.

Isobutanol, E2M, sodium hydrogen carbonate and tetrabutylammonium bromide were added in the container, further added with 15 ml of water, the temperature was raised to 65 degrees Celsius, sodium dithionite was added, allowing reacting for 30 minutes and then heating was ceased to stop the reaction to obtain a heated E2M aqueous solution.

2. An organic layer was taken out from the heated E2M aqueous solution, washed with water, dehydrated with anhydrous magnesium sulfate and then condensed and dried to obtain a powder from the condensed and dried organic layer.

With the method as demonstrated in the instant example, the molecular weight of donepezil is 379.5 and the yield of donepezil is 84.93% while the purity of the donepezil produced reaches 91.178%.

The reaction performed in the instant example is shown in Reaction 4.

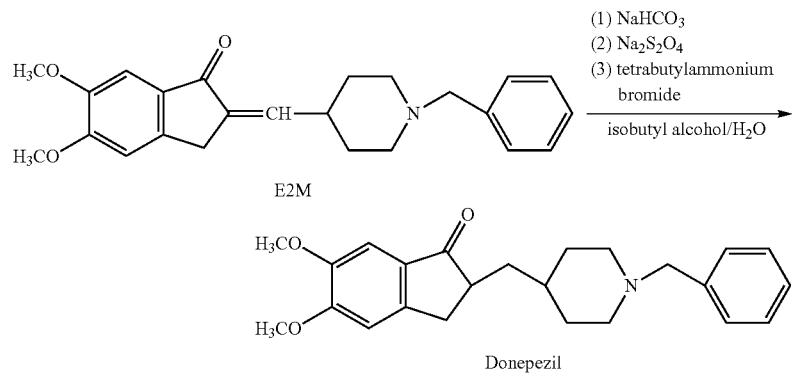

The following table 1 demonstrates the advantages of the present invention in comparison with conventional methods disclosed in a plurality of prior documents.

TABLE 1

| | Method | | | | | |
|---|---|---|---|---|---|---|
| | 1<br>Reagents | 2<br>Solvent | 3<br>Reaction time | 4<br>Yield | 5<br>Price of reagents | 6<br>Purity |
| Present invention | sodium hydrogen carbonate, sodium dithionite, tetrabutylammonium bromide | Methyl benzene/ water | 1 hour | More than 85.2% | Inexpensive | 99.756% |
| | sodium hydrogen carbonate, sodium dithionite, tetrabutylammonium bromide | Ethyl acetate/ water | 0.5 hour | More than 88.8% | Inexpensive | 99.802% |
| EP0296560, U.S. Pat. No. 5,100,901, U.S. Pat. No. 4,895,841 | Hydrogen gas, palladium/carbon | Tetrahydrofuran | 6 hours | More than 82% | Expensive | Not available |
| EP1939178, US2007088055, WO2007043440 | Hydrogen gas, palladium/aluminum oxide | Tetrahydrofuran | 3 hours | More than 90% | Expensive | 99.9% |
| US2010113793, WO2007108011 | Hydrogen gas, platinum/carbon | Ethyl acetate | 2 hours | More than 67% | Expensive | 99.93% |

TABLE 1-continued

| | Method | | | | | |
|---|---|---|---|---|---|---|
| | 1<br>Reagents | 2<br>Solvent | 3<br>Reaction time | 4<br>Yield | 5<br>Price of reagents | 6<br>Purity |
| EP1960357,<br>WO2007119118,<br>JP2009515945,<br>US2009253746 | Hydrogen gas,<br>platinum/carbon | Ethyl acetate | 7 hours | More than 47.6% | Expensive | 99.85% |

Example 5

The instant example demonstrates a method for making a derivate with donepezil made by the method in accordance with the present invention, e.g., donepezil hydrochloride. The method for making donepezil hydrochloride comprises the following steps:

1. Preparing donepezil by any of the methods described in examples 2 to 4;

2. Adding the donepezil into methanol to obtain a donepezil methanol solution;

3. Heating the donepezil methanol solution and adding concentrated hydrochloric acid to obtain a donepezil hydrochloride methanol solution; and 4. Adding diisopropyl ether to the donepezil hydrochloride methanol solution and lowering the temperature of the solution to facilitate formation of crystals therein, ice-bathing the solution and then filtering and vacuum-drying the solution to obtain donepezil hydrochloride.

In the instant example, the foregoing steps were specifically performed as follows:

1. 1.67 grams or 0.0044 mol of donepezil was added into 1.98 ml of methanol to obtain a mixture and the mixture was heated to 40 degrees Celsius to dissolve the donepezil in order to obtain a donepezil methanol solution.

2. 0.6 ml or 0.0053 mol of concentrated hydrochloric acid was added at the rate of 0.5 mL/min to the donepezil methanol solution to obtain a mixture. Filtration of the mixture was performed to obtain a filtered mixture.

3. 32.89 ml of diisopropyl ether was added to the filtered mixture to obtain a second mixture, the temperature was lowered at the rate of 3 degrees Celsius per 15 minutes so as to allow generation of crystals in the second mixture, and stirring of the second mixture was continued for 30 minutes until the temperature was lowered to room temperature.

4. The second mixture was ice-bathed at 5 to 10 degrees Celsius for 2 hours, filtration was performed to obtain a filter cake, the filter cake was washed with an icy solution having volumetrically equal amount of methanol and diisopropyl ether, and vacuum-drying was performed to obtain a white powder of donepezil hydrochloride, whose molecular weight was 416.

With the method as demonstrated in the instant example, the yield of donepezil hydrochloride is more than 90% while the purity thereof is 99.637%.

The reaction performed in the instant example is shown in Reaction 5.

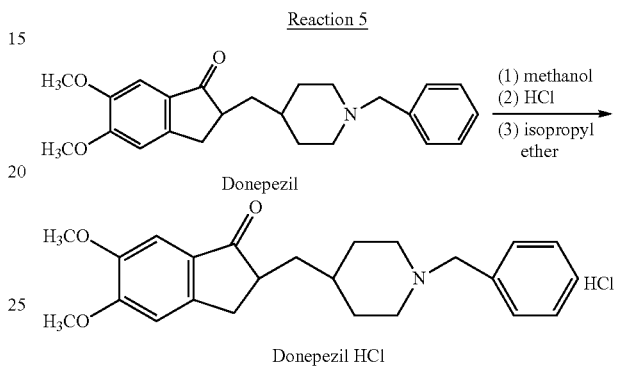

Reaction 5

Employing sodium dithionite as a reducing agent improves safety over hydrogen gas used in conventional methods and lowers the cost in contrast to the conventional noble metal catalysts that are extremely expensive. Furthermore, the method of the present invention requires only 60 minutes of reaction time to synthesize donepezil with a promising yield more than 85%, which greatly raises the efficiency and economic value of the manufacture of donepezil.

As described above, the method for making donepezil in accordance with the present invention is capable of overcoming the shortcomings and mitigating or obviating the problems of the prior art.

What is claimed is:

1. A method for making donepezil comprising:
   mixing (E)-2-((1-benzylpiperidine-4-yl)methylene)-5,6-dimethoxy-2,3-dihydro-1H-inden-1-one (hereinafter "E2M"), an organic solvent, a weak base, sodium dithionite, and a phase transfer catalyst to obtain an E2M mixture solution;
   heating the E2M mixture solution and adding water to obtain a heated E2M aqueous solution having an organic layer; and
   extracting the organic layer from the heated E2M aqueous solution, and condensing and drying the organic layer to obtain donepezil;
   wherein the weak base is sodium hydrogen carbonate,
   the phase transfer catalyst is tetrabutylammonium bromide; and
   the organic solvent is selected from the group consisting of:
   (a) methylbenzene, wherein the molar ratio of E2M:sodium hydrogen carbonate:sodium dithionite:tetrabutylammonium bromide is 1:18:9:0.5;
   (b) ethyl acetate, wherein the molar ratio of E2M:sodium hydrogen carbonate:sodium dithionite:tetrabutylammonium bromide is 1:6:2:0.5; and
   (c) isobutanol, wherein the molar ratio of E2M:sodium hydrogen carbonate:sodium dithionite:tetrabutylammonium bromide is 1:12:2:0.5.

2. The method as claimed in claim 1, wherein in the step of heating the E2M mixture solution and adding water to obtain a heated E2M aqueous solution having an organic layer, the E2M mixture solution is heated to 65 to 70 degrees Celsius and water is added to allow reacting for 30 to 60 minutes so as to obtain a heated E2M aqueous solution having an organic layer.

3. The method as claimed in claim 2, wherein the step of extracting the organic layer from the heated E2M aqueous solution, and condensing and drying the organic layer to obtain donepezil comprises:
- extracting the organic layer and washing the organic layer to obtain a washed organic layer; and
- dehydrating the washed organic layer with anhydrous magnesium sulfate, and condensing and drying the organic layer to obtain donepezil.

\* \* \* \* \*